United States Patent

Giannini et al.

(10) Patent No.: US 6,887,892 B2
(45) Date of Patent: May 3, 2005

(54) TRICYCLIC DERIVATIVES OF INDOLE WITH ANTIANGIOGENIC ACTIVITY

(75) Inventors: Giuseppe Giannini, Roma (IT); Mauro Marzi, Roma (IT); Maria Ornella Tinti, Roma (IT); Claudio Pisano, Roma (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 0 days.

(21) Appl. No.: 10/415,896

(22) PCT Filed: Oct. 16, 2001

(86) PCT No.: PCT/IT01/00526

§ 371 (c)(1), (2), (4) Date: Aug. 28, 2003

(87) PCT Pub. No.: WO02/36597

PCT Pub. Date: May 10, 2002

(65) Prior Publication Data

US 2004/0034052 A1 Feb. 19, 2004

(30) Foreign Application Priority Data

Nov. 3, 2000 (IT) .................................... RM2000A0570

(51) Int. Cl.⁷ ..................... A61K 31/403; C07D 403/04
(52) U.S. Cl. ........................ 514/411; 548/439; 548/421; 548/444; 514/410
(58) Field of Search ................................. 514/411, 410; 548/439, 421, 444

(56) References Cited

U.S. PATENT DOCUMENTS 5,350,762 A * 9/1994 Martin et al. ............... 514/411

FOREIGN PATENT DOCUMENTS

EP 0 496 314 A 7/1992
EP 0 614 888 A 9/1994

* cited by examiner

Primary Examiner—Charanjit S. Aulakh
(74) Attorney, Agent, or Firm—Nixon & Vanderhye P.C.

(57) ABSTRACT

Compounds of formula

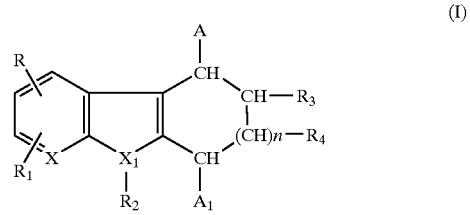

useful for treating tumors, particularly mammary carcinoma and colon carcinoma.

8 Claims, No Drawings

TRICYCLIC DERIVATIVES OF INDOLE WITH ANTIANGIOGENIC ACTIVITY

The invention described herein relates to compounds having tricyclic structure of the type tetrahydrociclopent[b] indole (1), tetrahydrocarbazole (2), and esahydrocycloept[b] indole (3), a processes for their preparations, and pharmaceutical composition containing the same for treating tumor and diseases associated with abnormal angiogenesis.

Said compounds have the following general formula (I):

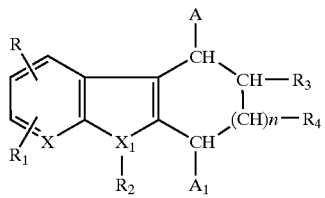

(I)

wherein:

X=CH, N $X_1$=O, S, N, CH

R and $R_1$, which may be the same or different, are selected from the group consisting of: —H, OH, $OR_5$ in which $R_5$ may be $C_1$–$C_4$ alkyl or benzyl, when two groups $OR_5$ are vicinal $R_5$ is methylene; or R and $R_1$ may be independently nitro; amino possibly mono- or di-substituted with $C_1$–$C_4$ alkyl; carboxy; alkoxy ($C_1$–$C_4$) carbonyl;

R and $R_1$ taken together may form an aliphatic or aromatic cyclic group having 5 or 6 atoms;

when $X_1$=N, CH, then $R_2$ is selected from the group consisting of —H, phenyl, benzyl, linear or branched $C_1$–$C_6$ alkyl;

n=is an integer ranging from 0 and 4;

$R_3$, which may be the same as or different from $R_4$, may be: —H, —OH, —$OR_6$, wherein $R_6$ is linear or branched $C_1$–$C_4$ alkyl, or when $R_3$=$R_4$= $OR_6$ vicinal, $R_6$ is isopropylidene

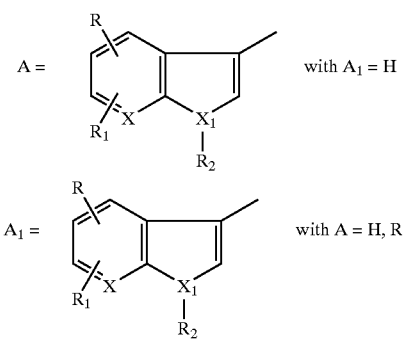

$R_7$=$C_1$–$C_4$ linear or branched alkyl possibly substituted with one or two groups OH, $OR_6$, in case of 2 groups $OR_6$ vicinal, $R_6$ is isopropyliden; or $R_7$ is formyl (CHO), oxime (CH=NOH).

The invention includes all the possible isomers, stereoisomers and their mixtures, metabolites and their metabolic precursors or bio-precursors (so called pro-drug) of the general formula.

The use of antineoplastic drugs in human therapy causes a substantial number of toxic or side effects which consequently lead to a reduction of the amount of drug to be administered, and in some cases to discontinuation of the therapy. A reduction of the amount of drug to be administered or discontinuation of the therapy cause an increase in primary tumour growth and/or the occurrence of tumour metastases.

The growth of a primary tumour is favoured by good vascularisation (by angiogenesis) of the tumour tissue. An adequate supply of oxygen and nutrients promotes rapid growth of the tumour itself. It has been demonstrated that the extent of angiogenesis can be an extremely negative factor in the prognosis of neoplasms.

Angiogenesis in the adult is normally quiescent, but it represents a normal function, for example in the healing of wounds, or in the reconstruction of the endometrium during the female reproductive cycle.

The angiogenic response is physiologically stimulated when the vascular functions are reduced and tissue perfusion is inadequate.

More generally, it can be claimed that, in physiological conditions, angiogenesis constitutes a positive feedback in response to inadequate perfusion, or to a reduced supply of oxygen and nutrients, such as occurs, for instance, in the case of occlusion of an artery, in situations of tissue mass growth (for example, the neovascularisation that accompanies the formation of muscle tissue); and in the case of an increased work load in association with an increased oxygen and nutrient requirement.

In the course of local ischaemia, due to partial or complete occlusion of an artery, the development of collateral vessels is necessary in order to maintain perfusion.

As above mentioned, it has been demonstrated that the extent of angiogenesis can be an extremely negative factor in the prognosis of neoplasms (van Hinsbergh V W, Collen A, Koolwijk P; Ann. Oncol., 10 Suppl., 4:60–3, 1999; Buolamwini J K; Curr. Opin. Chem. Biol., 3(4):500–9, 1999 August).

It is also known, in the neoplastic field, that a fundamental stage in the biology of the tumour cell is the acquisition of metastasising capability.

The tumour cells that metastasise are able to lose adherence to the surrounding structures, invade blood and lymphatic vessels and colonise other tissues at a distance where they can continue to reproduce themselves.

Metastasising is also a critical event in the clinical history of the disease, being the main cause of death due to cancer. It is closed associated with and facilitated by the presence of vascular tissue in the tumour site or adjacent areas.

The migration of tumour cells across the surrounding structures enables the cells to reach the intratumoural blood vessels, whether pre-existing or formed by neo-angiogenesis, and thus reach the bloodstream (Ray J M., Stetler-Stevenson W G; Eur. Respir. J., 7(11):2062–72, 1994; Stetler-Stevenson W G, Liotta L A, Kleiner D E Jr.; FASEB J., 7(15):1434–41, 1993 December).

The presence of communication between lymphatic and blood vessels in the vascular region of the tumour enables the neoplastic cells to move in both vascular systems.

Recent studies have shown a direct relationship between angiogenesis and arthritic disease (Koch A E; Arthritis and Rheumatism 41:951–962, 1998). In particular, it has been demonstrated that neo-vascularisation of the articular cartilages plays a crucial role in pannus formation and in progression of arthritis. A normal cartilage does not possess blood vessels, while the synovial fluid of arthritic patients contains an angiogenesis-stimulating factor produced by endothelial cells (EASF).

The presence of this factor is associated with vascularisation and degradation of the cartilage.

Other diseases are also related to abnormal angiogenesis.

It has been found that, in diabetic retinopathy [Histol. Histopathol. 1999 October; 14(4):1287–94], psoriasis [Br J. Dermatol. 1999 December; 141(6):1054–60], chronic inflammation and arteriosclerosis [Planta Med. 1998 December; 64(8):686–95], neovascularisation of the affected tissues is a facilitating factor.

Over the past thirty years compounds with a cycloalkanoindole structure have been synthesised and studied with a view to exploiting their possible therapeutic potential.

The basic requisite of these compounds—the substituted indole in position 3—is a feature shared by natural products such as melatonin or tryptophan.

In the '70s, cycloalkanoindole compounds were studied for their antiinflammatory properties (J. Med. Chem. 1976, 19(6):787–92) or for their antidepressant properties (J. Med. Chem. 1976, 19(6):792–7).

These studies were then followed by others (on a number of aminotetrahydrocarbazols) to assess their effects on the CNS (J. Med. Chem. 1977, 20(4):487–92) in that they possessed a tryptamine-like structure.

In the '80s, a number of derivatives with a tetrahydrocarbazol structure were found to possess antibacterial properties: in culture they inhibit the growth of *Trypanosoma cruzi* (Rev. Argent. Microbiol. 1987, 19(3):121–4).

In the '90s, compounds with a cycloalkanoindole structure were studied as potential analgesics (Xenobiotica 1989, 19(9):991–1002), with effects on the serotonin receptors (J. Med. Chem. 1993, 36(13): 1918–9) and on the melatonin receptors (Eur. J. Pharmacol. 1995, 287(3):239–43).

In the past few years, tetrahydrocarbazol derivatives have been studied for their antiproliferative properties (Farmaco 1998, 53(6):431–7); in particular, the N-pyridinium derivative may act with a mechanism involving inhibition of topoisomerase II.

U.S. Pat. No. 5,017,593 describes derivatives of cyclohept[b]indole alkanoic acid as leukotriene antagonists.

EP 0496237 describes N-imidazolyl derivatives of tetrahydrocarbazol and cyclohept[b]indoles as thromboxane antagonists (TXA-2), useful in the treatment of cardiovascular disorders (myocardial infarction and angina), cerebrovascular disease (stroke, transient ischaemic attacks, migraine), peripheral vascular disease (microangiopathy), kidney disease (glomerular sclerosis, lupus nephritis, diabetic nephropathy), respiratory disease (bronchoconstriction and asthma) and atherosclerosis.

J. Med. Chem. 1998, 41, 451–67 describes compounds with tetrahydrocyclopent[b]indole (1), tetrahydrocarbazol (2), and hexahydrocyclohept[b]indole (3) structures used for studies on melatonin receptors having formula:

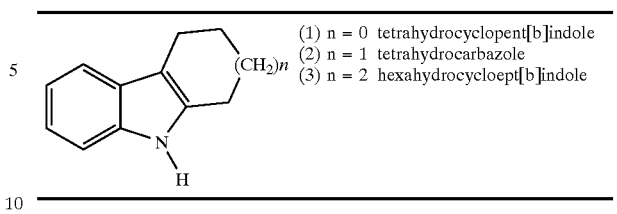

U.S. Pat. No. 5,830,911; U.S. Pat. No. 4,927,842; U.S. Pat. No. 4,616,028 describe tetrahydrocarbazol compounds, with antiinflammatory activity having formula:

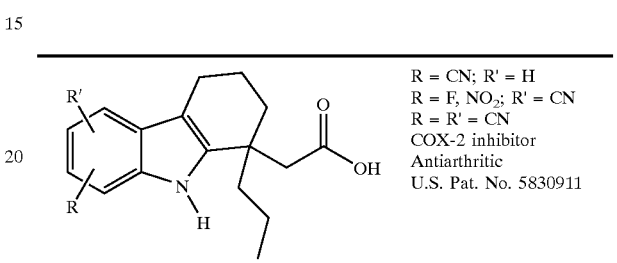

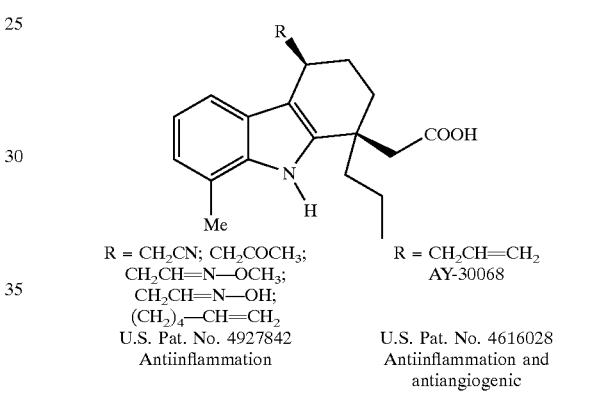

The compounds described in the above cited publications are different from those claimed in the present invention.

Despite the progress made in recent years, the pharmacological research concerned with discovering new drugs for the treatment of tumor diseases and diseases characterised by abnormal angiogenesis is still considered by many experts in medicine as one of the most promising field.

In fact, to date there is still a strongly perceived need for new compounds capable of blocking or interfering with the tumour diseases and diseases caused by abnormal angiogenesis. As mentioned above, these diseases include tumours, tumours metastasis, arthritic diseases, diabetic retinopathy, psoriasis, chronic inflammation and arteriosclerosis.

It has now been found that the formula (I) compounds, characterised by the presence of two aromatic bases (indole or one of its derivatives), where the first is condensed to a saturated cycle in position 2–3, of the tetrahydrocarbazol type, and the second aromatic base, bound in position 3, is present as a substituent in the benzyl position of the saturated ring, unexpectedly possess antitumor and antiangiogenic properties.

Compounds with general formula (I) are therefore the object of the invention described herein.

A further object of the invention described herein are compounds with general formula (I) and their use in the medical field.

A further object of the invention described herein are compounds with general formula (I) and a process for their preparation.

A further object of the invention described herein is a pharmaceutical composition containing as active ingredient a formula (I) compound and at least a pharmaceutically acceptable excipient and/or diluent.

A further object of the invention described herein is a pharmaceutical composition containing as active ingredient a formula (I) compound, for the treatment of a tumour pathology, in which the tumour is selected from the group consisting of sarcoma, carcinoma, carcinoid, bone tumour, neuroendocrine tumour, lymphoid leukaemia, acute promyelocytic leukaemia, myeloid leulaemia, monocytic leukaemia, megakaryoblastic leukaemia and Hodgkin's disease.

A further object of the invention described herein is the use of compounds of formula (I) for the preparation of a medicament with antiangiogenic activity.

A further object of the invention described herein is the use of compounds of formula (I) for preventing the onset of tumour metastases.

A further object of the invention described herein is the use of compounds of formula (I) for the treatment of arthritic disease.

A further object of the invention described herein is the use of compounds of formula (I) for the treatment of diabetic retinopathy.

A further object of the invention described herein is the use of compounds of formula (I) for the treatment of psoriasis.

A further object of the invention described herein is the use of compounds of formula (I) for the treatment of chronic inflammatory diseases.

A further object of the invention described herein is the use of compounds of formula (I) for the treatment of arteriosclerosis.

As mentioned above, the growth of a primary tumour is facilitated by good vascularisation of the tumour tissue, and the extent of the neoangiogenesis may be a highly adverse factor in the prognosis of neoplasms. An adequate supply of oxygen and nutrients in the tumour site, in fact, facilitates rapid growth of the tumour itself.

It is well known that the therapeutic measures available to physicians for the treatment of tumours are still unable to prevent many patients from dying of these diseases. It is also well known that most oncological patients are treated not with a single anticancer drug but with a combination of several anticancer agents. The need to administer anticancer drugs in combination stems from the fact that by acting at different metabolic levels in some cases they favour complete remission of the tumour, while in others they lengthen the patient's life and/or improve the quality of life of the patients treated.

To date there is still a strongly perceived need for new compounds to be used in combination with known compounds in the fight against cancer.

The compound according to the invention described herein can be used in combination with one or more anticancer drugs.

A further object of the invention described herein is the combination of compounds of formula (I) with one or more known anticancer drugs.

A further object of the invention described herein is a pharmaceutical composition containing the combination of compounds of formula (I) with one or more known anticancer drugs, and one or more excipients or vehicles pharmacologically acceptable.

A further object of the invention described herein is a pharmaceutical composition containing as active ingredient a formula (I) compound, in combination with one or more known antitumour compounds, in which the antitumour compound is selected from the group consisting of alkylating agents, topoisomerase inhibitors, antitubulin agents, intercalating compounds, anti-metabolites, natural products such as vinca alkaloids, epipodophyllotoxins, antibiotics, enzymes, taxans, and cyto-differentiating compounds.

A further object of the invention described herein is the use of the combination of compounds of formula (I) and the anticancer compound to prepare a medicament for the treatment of tumour, characterised in that the compound of formula (I) is present as a coadjuvant of the anticancer compound.

The following examples illustrate the invention

The synthesis of cyclised products consists of two stages: the first stage consists in the condensation, in the geminal position, of a hydroxyaldehyde with 2 aromatic bases; the second stage consists in a cyclisation reaction with DAST (diethyl amino-sulphur trifluoride). This synthetic sequence, albeit with exceptions, may represent the synthesis process adopted in the preparation of all the derivatives described herein. For the sake of simplicity of description, the case of formula (I) compounds where dove X is CH, $X_1$ is NH, and $R_3$ and $R_4$ are hydrogen is illustrated. It is perfectly clear that the expert in the sector can prepare all the formula (I) compounds using suitable starting materials and adopting suitable reagents, simply by availing himself or herself of his own general knowledge, or with the aid of the standard manuals available.

1° STEP

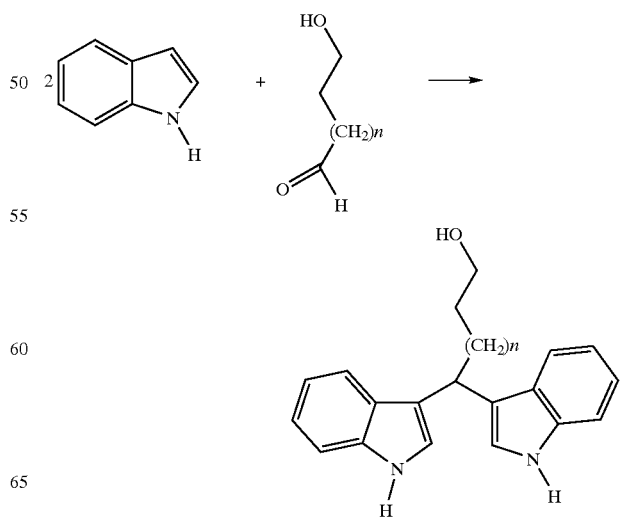

2° STEP

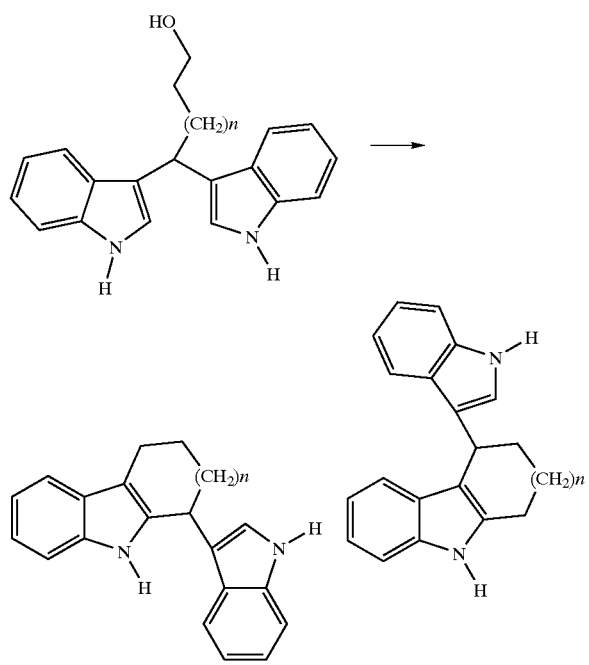

As the expert in the sector will readily appreciate, the first stage in the synthesis involves the preparation of intermediate products with a bisindole structure.

Their preparation can be done using various different methods.

PROCEDURE A: Synthesis of Derivatives with Mannofuranose

Scheme (1)

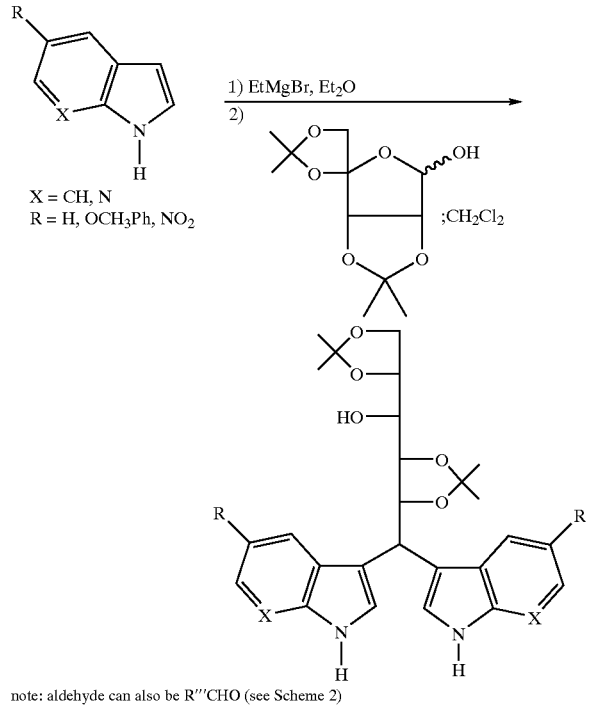

note: aldehyde can also be R'''CHO (see Scheme 2)

Reaction (Tetrahedron Asymmetry, 1997, 8(17), 2905–12): The indole or its derivatives (1 mmol) was dissolved in $Et_2O$ anhydrous (50 ml). A solution of ethylmagnesiumbromide/ether (3M) (0.33 ml; 1 mmol) was slowly added. The solution so obtained was left under stirring, in anhydrous conditions, for several minutes: a magnesium white salt derivative was obtained. The ether was evaporated the white residual obtained was dissolved in anhydrous $CH_2Cl_2$. The solution was left at room temperature/reflux for 12/36 h.

Work-up: the solution was quenched by addition of a saturated solution of $NaHCO_3$/10% $NH_4Cl$. The organic phase was separated and dried on $Na_2SO_4$ and evaporated. The desired product was purified by flash chromatography (hexane/acetone).

PROCEDURE B: Synthesis of Hydroxyaldeide Derivatives

Scheme (2)

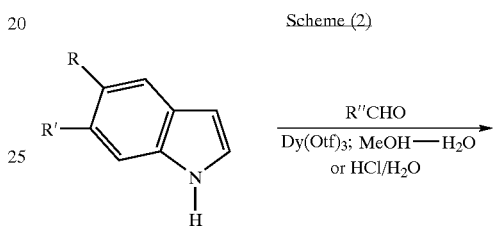

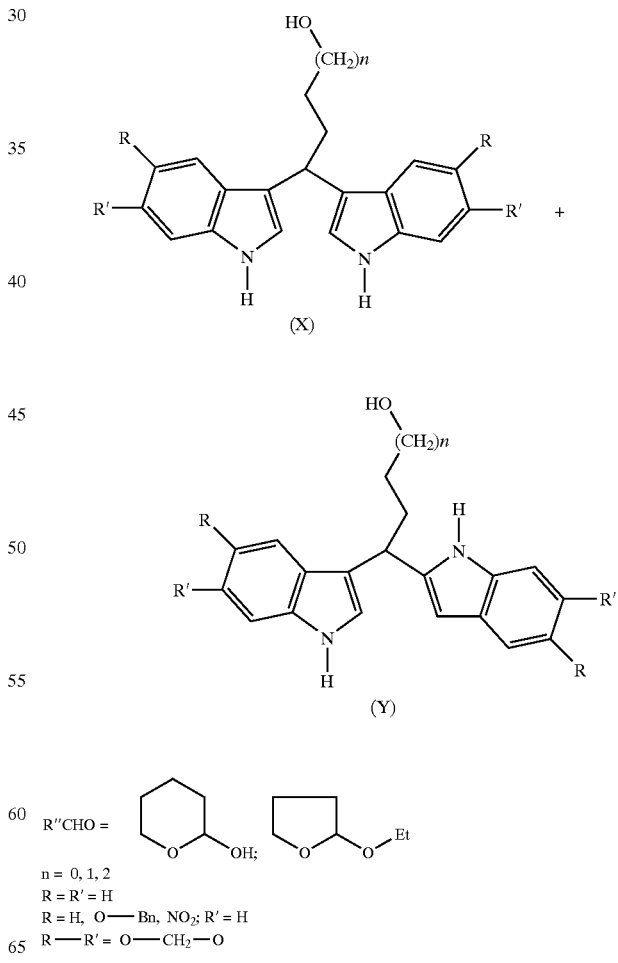

n = 0, 1, 2
R = R' = H
R = H, O—Bn, $NO_2$; R' = H
R—R' = O—$CH_2$—O

Reaction: the indole or its derivative (2 mmol) was dissolved with the aldehyde (5-hydroxy-pentanale or 2-etoxytetrahydrofurano) (1 mmol), in 15 ml of MeOH/H$_2$O (2/1). finally Dysprosium triflate was added and the mixture was left to react at room temperature/80° C. for 6/36 h.

Work-up: The reaction mixture was quenched with 10% NaHCO$_3$, extracted with CH$_2$Cl$_2$. The extracted were dried Na$_2$SO$_4$, and evaporated. The raw residual was purified by preparative-HPLC and two regioisomers were isolated (X) and (Y).

Procedure C: Reaction of Cyclization on Mannofuranose Derivatives

Scheme (3)

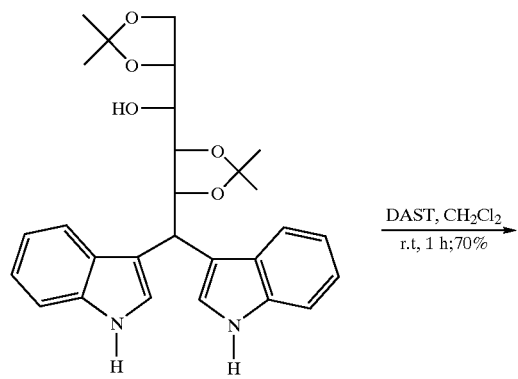

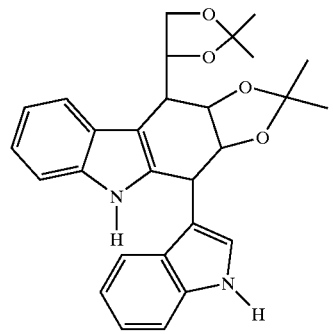

Reaction: The bis-indolyl derivative (476 mg; 1 mmol) was dissolved in CH$_2$Cl$_2$ (80 ml). At the solution was added, at room temperature, diethylaminosulfur trifluoride (DAST) (400 µl; 3 mmol). The reaction was rapid.

Work-up: after 60' a solution of 10% NaHCO$_3$ was added, and the solution was extracted with CH$_2$Cl$_2$. The organic extracted were dried on Na$_2$SO$_4$ and evaporated. The reaction products present in this raw reaction product were isolated by preparative-TLC or better by preparative-HPLC RP-18.

Procedure D: Reaction of Cyclization on Derivatives with Hydroxyaldehyde

Scheme (4)

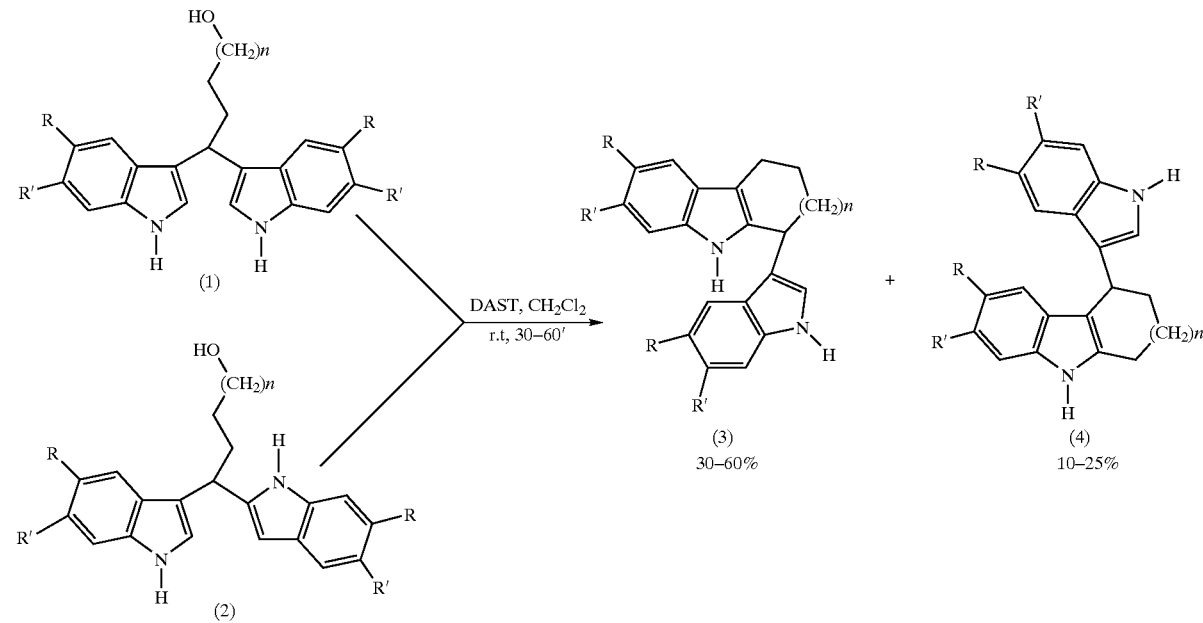

n = 0, 1, 2
R = H, O—Bn, NO$_2$
R' = H
R—R' = O—CH$_2$—O

Reaction: the symmetric derivative (1) or asymmetric derivative (2) (1 mmol) was dissolved in CH$_2$Cl$_2$ (20 ml). DAST (200 µl; 1.5 mmol) was added to the solution, at 0° C.—room temperature. The reaction was rapid. After 15'–20' the starting product was almost completely reacted.

Work-up: after 30' a solution of 10% NaHCO$_3$ was added, the solution so obtained was extracted with CH$_2$Cl$_2$. The organic extracted were dried on Na$_2$SO$_4$ and evaporated. The reaction products present in this raw reaction product were isolated by preparative-TLC or better by RP-18 prep.-HPLC.

Starting from the symmetric or from the non-symmetric product were formed both, the derivative with the second indole residual toward the lower part (3) with a yield of 30–60% and the derivative with the indole residual toward the high part (4): the latter is present in 10–25% respect to the other.

-continued

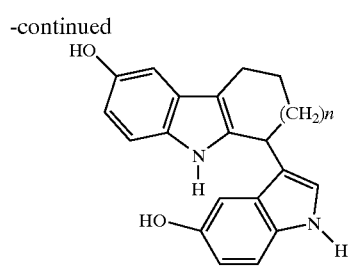

Reaction: the benzylated derivative (1 mmol) was dissolved in CH$_3$OH (50 ml)

The catalyst (10% Pd/C; 30 mg) was added to the solution, at room temperature.

The solution so obtained was left under hydrogen (60 psi). After 16 h the starting product was completely reacted.

Work-up: The catalyst was filtered of. The organic phase was evaporated. The deprotected product was purified by flash-chromatography. Yield 85%.

Procedure F: Deprotection Reaction

Scheme (6)

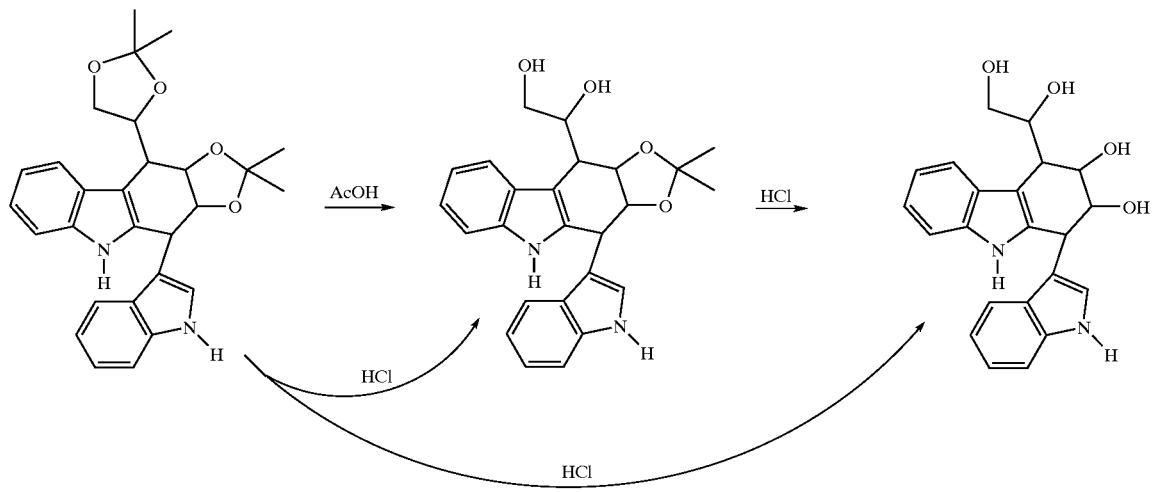

Procedure E: Debenzylation Reaction

Scheme (5)

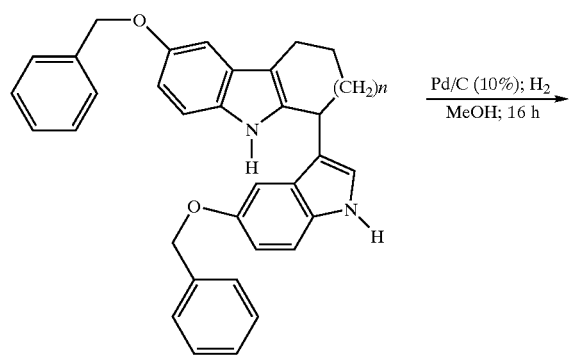

Reaction: the protect product (1 mmol) was dissolved in tetrahydrofuran (THF) (50 ml). HCl 1N was added to the solution. The solution so obtained was left for 1 h at 20° C.–40° C. So the starting product was completely reacted. The principal deprotect product obtained was the desired product.

With reference to the deprotected product only in the esocyclic residual, the deprotection can be obtained by acid hydrolysis at low temperature (ex. 1N HC at low temperature, for 30'–60').

Work-up: the obtained product (vedi es. 1) was shacked with a saturated solution of NaHCO$_3$. The THF was evaporated, then the product was extracted with AcOEt. The organic phase was evaporated end the deprotected product was purified by flash-chromatography.

Yield 85%.

Procedure G: Oxydation Reaction.

Scheme (7)

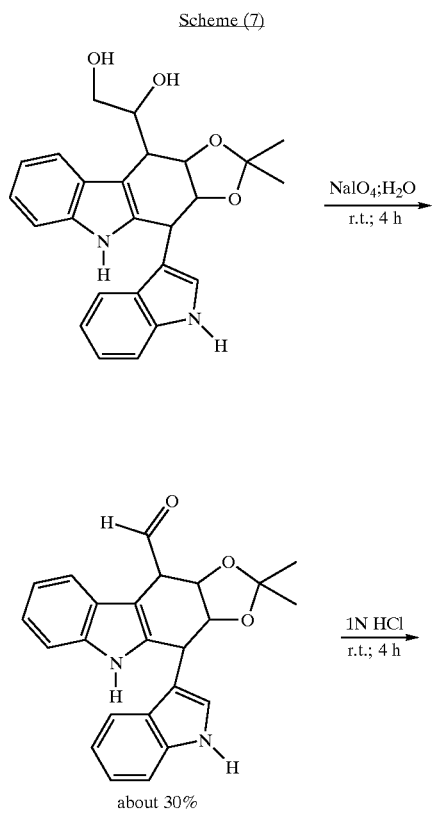

about 30%

Reaction: The aldehyde (1 mmol) was dissolved in 20 mL of MeOH. To the solution was added NaIO4 (1 mmol) dissolved in 2 mL of H₂O.

The solution so obtained was left at room temperature for 4 h.

Work-up: 1° Step: a Na₂S₂O₃ aqueous solution was added. The organic solvent was evaporated and the residual was extracted with AcOEt.

2° Step: the protect intermediate can be deprotected as described in scheme 6.

EXAMPLE 1

ST 1345

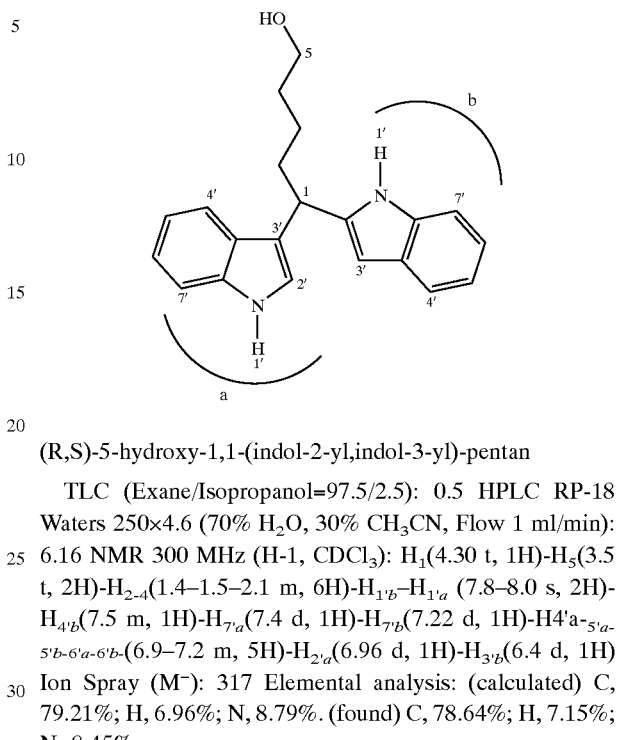

(R,S)-5-hydroxy-1,1-(indol-2-yl,indol-3-yl)-pentan

TLC (Exane/Isopropanol=97.5/2.5): 0.5 HPLC RP-18 Waters 250×4.6 (70% H₂O, 30% CH₃CN, Flow 1 ml/min): 6.16 NMR 300 MHz (H-1, CDCl₃): $H_1$(4.30 t, 1H)-$H_5$(3.5 t, 2H)-$H_{2-4}$(1.4–1.5–2.1 m, 6H)-$H_{1'b}$–$H_{1'a}$ (7.8–8.0 s, 2H)-$H_{4'b}$(7.5 m, 1H)-$H_{7'a}$(7.4 d, 1H)-$H_{7'b}$(7.22 d, 1H)-$H4'a$-$_{5'a\text{-}5'b\text{-}6'a\text{-}6'b}$(6.9–7.2 m, 5H)-$H_{2'a}$(6.96 d, 1H)-$H_{3'b}$(6.4 d, 1H) Ion Spray (M⁻): 317 Elemental analysis: (calculated) C, 79.21%; H, 6.96%; N, 8.79%. (found) C, 78.64%; H, 7.15%; N, 8.45%.

EXAMPLE 2

ST 1346

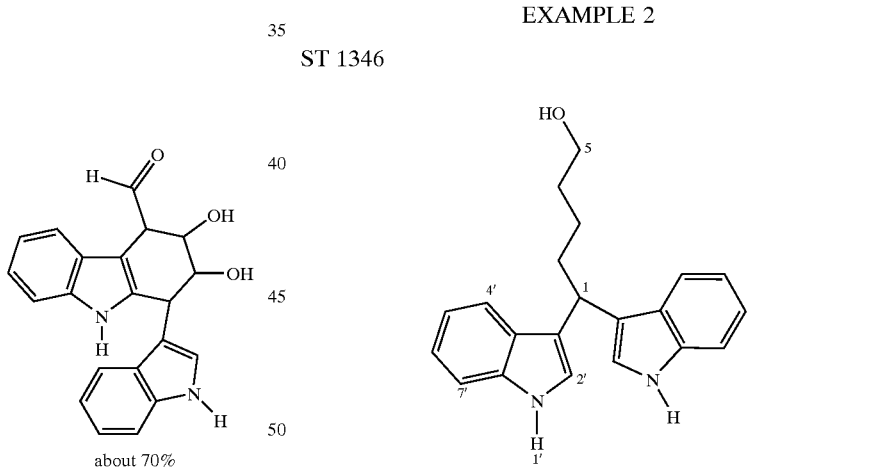

5-Hydroxy-1,1-di-(indol-3-yl)-pentane

TLC (Exane/iPrOH=97.5/2.5): 0.43 HPLC RP-18 Waters 250×4.6 (40% H₂O, 60% CH₃CN, Flow 1 ml/min): 5.36 NMR 300 MHz (H-1, CDCl₃): $H_1$(4.7 t, 1H)-$H_5$(3.8 t, 2H)-$H_4$(2.3 m, 2H)-$H_3$(1.7 m, 2H)-$H_2$(1.8 m, 2H)-$H_{2'}$(7.2 s, 2H)-$H_{5'}$(7.15 t, 2H)-$H_{6'}$(7.4 t, 2H)-$H_{4'}$(7.5 d, 2H)-$H_{7'}$(7.8 d, 2H)-$H_{1'}$(8.15 br.s, 2H) NMR 300 MHz (C-13, CDCl₃): $C_1$(34.2)-$C_2$(33.0)-$C_3$(24.6)-$C_4$(35.7)-$C_5$(63.2)-$C_{7'}$(111.2)-$C_{6'}$(119.2)-$C_{4'}$(119.8)-$C_{3'}$(120.4)-$C_{5'}$(121.6)-$C_{2'}$(122)-$C_{3'bis}$(127.2)-$C_{7'bis}$(136.7) Ion Spray (M⁻): 317 Elemental analysis: C, 79.21%; H, 6.96%; N, 8.79%. found C, 78.70%; H, 7.29%; N, 8.39%. Melting point: 190° C. (dec)

EXAMPLE 3

ST 1422

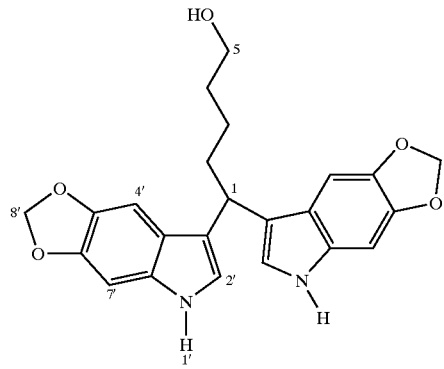

5-hydroxy-1,1-di-(5,6-methylendioxy-indol-3-yl)-pentane

TLC (Hexane/iPrOH=97.5/2.5): 0.55 HPLC RP-18 (50% $H_2O$, 50% $CH_3CN$, Flow 1 ml/min): 6.7 NMR 300 MHz (H-1, $CD_3CN$): $H_1$(4.2 t, 1H)-$H_2$(2.2 m, 2H)-$H_3$-$H_4$(1.4–1.5 m, 2H)-$H_5$(3.4 q, 2H)-$H_{8'}$(5.8 s, 4H)-$H_{4'}$-$H_{7'}$(6.8 s, 4H)-$H_{2'}$ (7.0 s, 2H)-$H_{1'}$(8.9, brs, 2H) Ion Spray ($M^+$): 407 Elemental analysis: C, 67.97%; H, 5.46%; N, 6.89%. found in accordance with the theoretical. Melting point: 200° C. (dec.)

EXAMPLE 4

ST 1423

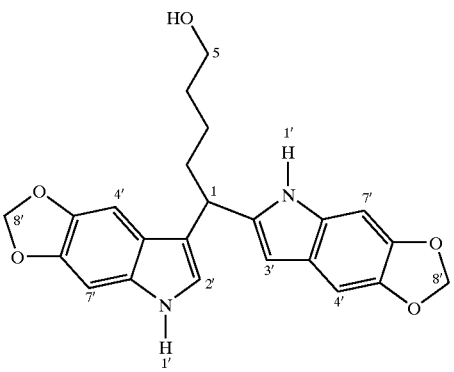

(R,S)-5-hydroxy-1,1-di-(5',6'-methylendioxy-indol-2-yl,5'', 6''-methylendioxy-indol-3-yl)-pentane TLC (Hexane/iPrOH=97.5/2.5): 0.63 HPLC RP-18 (50% $H_2O$, 50% $CH_3CN$, Flow 1 ml/min): 8.2 NMR 300 MHz (H-1, $CD_3CN$): $H_1$(4.3 t, 1H)-$H_2$(2.2 m, 2H)-$H_3$-$H_4$ (1.4–1.6 m, 4H)-$H_5$(3.5 m, 2H)-$H_{8'a-8'b}$ (5.9 s, 4H)-$H_{3'b}$(6.3 s, 1H)-$H_{4'a}$-$H_{7'a}$ (6.8–6.9 d, 2H)-$H_{4'b}$-$H_{7'b}$ (7.0 d, 2H)-$H_{2'a}$ (7.2 s, 1H)-$H_{1'a-1'b}$(8.9–9.1 brs-brs, 2H). NMR 300 MHz (C-13, $CD_3CN$): 25.1-33.4-34.9-37.2-62.5-92.6-93.0-98.4-99.2-99.7-101.3-101.5-121.7 Ion Spray ($M^+$): 407 Elemental analysis: (calculated) C, 67.97%; H, 5.46%; N, 6.89%. (found) in accordance with the theoretical. Melting point: 220° C. (dec.)

EXAMPLE 5

ST1730

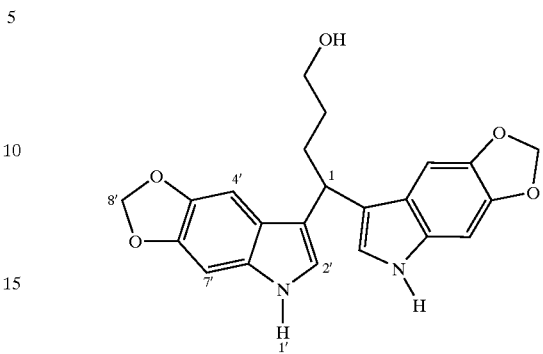

4-hydroxy-1,1-di-(5',6'-methylendioxy-indol-3-yl)-butane

TLC (Hexane/iPrOH=75/25): 0.44 HPLC RP-18 (60% $H_2O$, 40% $CH_3CN$, Flow 1 ml/min): 17.5 NMR 300 MHz (H-1, $CD_3CN$): $H_1$(4.3 t, 1H)-$H_2$(2.3 m, 2H)-$H_3$(1.6 m, 2H)-$H_4$(3.6 q, 2H)-$H_{8'}$(6.0 s, 4H)-$H_{4'}$-$H_{7'}$(6.9 s, 4H)-$H_{2'}$(7.2 s, 2H)-$H_{1'}$(9.0 brs, 2H) Ion Spray ($M^+$): 393 Elemental analysis: C, 67.34%; H, 5.14%; N, 7.14%. (found): in accordance with the theoretical. Melting point: 240° C. (dec.)

EXAMPLE 6

ST1731

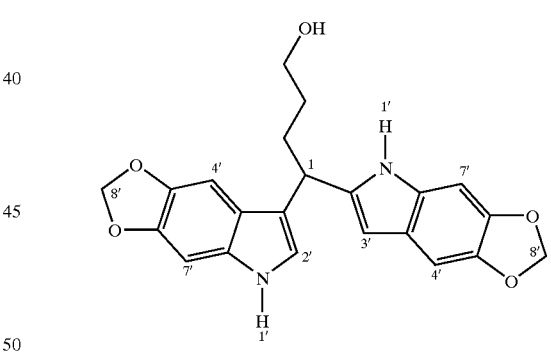

(R,S)-4-hydroxy-1,1-di-(5',6'-methylendioxy-indol-2-yl,5'', 6''-methylendioxy-indol-3-yl)-butane TLC (Hexane/iPrOH=75/25): 0.41 HPLC RP-18 (60% $H_2O$, 40% $CH_3CN$, Flow 1 ml/min): 23.4 NMR 300 MHz (H-1, $CD_3CN$): $H_1$(4.3 t, 1H)-$H_2$(2.2 m, 2H)-$H_3$(1.6 m, 4H)-$H_4$(3.7 m, 2H)-$H_{8'a-8'b}$ (6.0 s, 4H)-$H_{3'b}$(6.4 s, 1H)-$H_{4'a}$-$H_{7'a}$ (6.8–6.9 d, 2H)-$H_{4'b}$-$H_{7'b}$ (7.0 d, 2H)-$H_{2'a}$(7.2 s, 1H)-$H_{1'a-1'b}$(8.9–9.1 brs-brs, 2H) NMR 300 MHz (C-13, $CD_3CN$): 29.8-30.4-35.5-60.8-90.9-91.4-96.7-97.5-98.1-99.6-99.9-116.6-116.9-119.9-121.6-130.0-130.9-141.3-141.5-141.6-142.9-143.8 Ion Spray ($M^-$): 391 Elemental analysis: (calculated): C, 67.34%; H, 5.14%; N, 7.14%. (found): in accordance with the theoretical. Melting point: 205° C. (dec.)

EXAMPLE 7

ST 1707

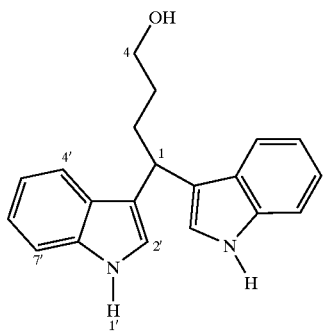

1,1-di(indol-3-yl)-4-hydroxy-butane

TLC (Hexane/AcOEt=1/1): 0.26 HPLC RP-18 (50% $H_2O$, 50% $CH_3CN$, Flow 1 ml/min): 8.3 NMR 300 MHz (H-1, $CD_3CN$): $H_1$(4.3 t, 1H)-$H_2$(2.2 m, 2H)-$H_3$(1.4 m, 2H)-$H_4$(3.4 t, 2H)-$H_{2'}$(7.2 s, 2H)-$H_5$(6.8 t, 2H)-$H_6$(6.9 t, 2H)-$H_{4'}$(7.2 d, 2H)-$H_7$(7.5 d, 2H)-$H_{1'}$(10.7 br.s, 2H) NMR 300 MHz (C-13, $CD_3CN$): $C_1$(61.5)-$C_{2-3}$(32.2)-$C_4$(34)-$C_{7'}$(112)-$C_{6'}$(118.5)-$C_{3'}$-$C_{4'}$(119.5–119.7)-$C_5$(121.2)-$C_{2'}$(121.6)-$C_{3'bis}$(127.4)-$C_{7'bis}$(137.1) Ion Spray (M$^-$): 303 Elemental analysis: (calculated) C, 78.92%; H, 6.62%; N, 9.20%. (found) in accordance with the theoretical. Melting point: 110–115° C.

EXAMPLE 8

ST 1750

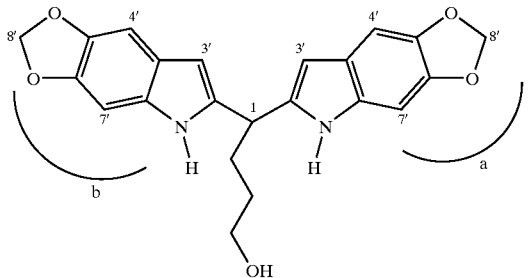

4-hydroxy-1,1-di-(5',6'-methylendioxy-indol-2-yl)-butane

TLC (Hexane/iPrOH=75/25): 0.60 HPLC RP-18 (60% $H_2O$, 40% $CH_3CN$, Flow 1 ml/min): 19.9 NMR 300 MHz (H-1, $CD_3CN$): $H_1$(4.3 t, 1H)-$H_2$(2.3 m, 2H)-$H_3$(1.6 m, 2H)-$H_4$(3.6 q, 2H)-$H_8$(6.0 s, 4H)-$H_{4'}$-$H_{7'}$(6.9–7.0 2s, 4H)-$H_{3'}$(6.4 s, 2H)-$H_{1'}$(9.1 brs, 2H) Ion Spray (M$^-$): 391 Elemental analysis: C, 67.34%; H, 5.14%; N, 7.14%. (found): in accordance with the theoretical. Melting point: 250° C. (dec.)

EXAMPLE 9

ST 1866

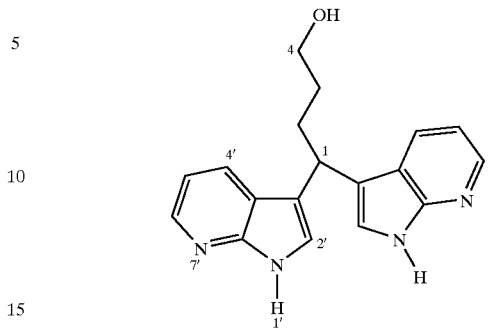

1,1-di(7'-aza-indol-3-yl)-4-butanol

TLC (Hexane/AcOEt=75/25): 0.18 HPLC RP-18 (60% $H_2O$, 40% $CH_3CN$, Flow 1 ml/min): 4.4 NMR 300 MHz (H-1, $CD_3OD$): $H_1$(4.4 t, 1H)-$H_2$(2.3 m, 2H)-$H_3$(1.6 m, 2H)-$H_4$(3.6 t, 2H)-$H_{2'}$(7.3 s, 2H)-$H_5$(6.9 m, 2H)-$H_{4'}$(8.1 t, 2H)-$H_6$(7.8 d, 2H) NMR 300 MHz (C-13, $CD_3CN$): 30.3-30.7-33.6-61.0-114.0-117.2-119.4-121.9-127.5-140.9-147.7 Ion Spray (M$^-$): 305 Elemental analysis: (calculated) C, 70.57%; H, 5.92%; N, 18.29%. (found) in accordance with the theoretical. Melting point: 221° C. (dec.)

EXAMPLE 10

ST 1372

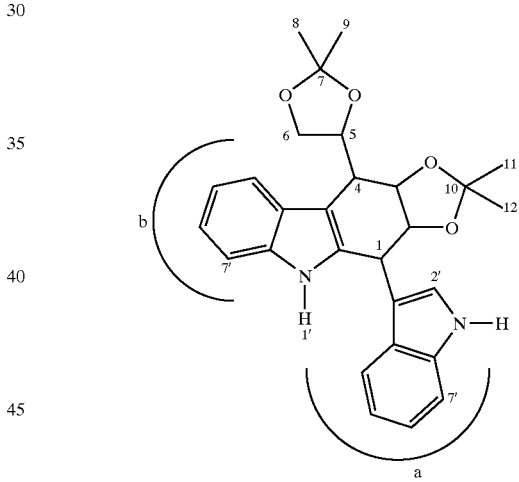

1-(indol-3-yl)-2,3-O-isopropylidene-4-(2,3-O-isopropylidene-ethyl)-tetrahydrocarbazole TLC (Hexane/Acetone=8/2): 0.75 HPLC RP-18 Waters 300×3.3(40% $H_2O$, 60% $CH_3CN$, Flow 1 ml/min): 12.8

Racemic Mixture

NMR 300 MHz (H-1, $CH_3CN$): $H_1$+$H_3$ (4.52 m, 2H)-$H_2$ (4.64 m, 1H)-$H_4$(3.66 m, 1H)-$H_5$(4.67 m, 1H)-$H_6$(3.97/3.69 m, 2H)-$H_8$(1.42 s, 3H)-$H_9$(1.32 s, 3H)-$H_{11}$(1.46 s, 3H)-$H_{12}$(1.38 s, 3H)-$H_{2'a}$(6.94 s, 1H)-$H_{4'a}$(7.51 d, 1H)-$H_{4'b}$(7.69 d, 1H)-$H_{6'a}$(7.16 m, 1H)-$H_{6'b}$(7.09 m, 1H)-$H_{7'a}$(7.47 d, 1H)-$H_{7'b}$(7.26 d, 1H)-$H_{1'a}$(9.0 s, 1H)-$H_{1'b}$(8.3 s, 1H) NMR 300 MHz (C-13, $CH_3CN$): $C_1$(38.15), $C_2$(80.77), $C_3$(75.9), $C_4$(40.77), $C_5$(78.0), $C_6$(68.33), $C_8$(25.5), $C_9$(26.8), $C_{11}$(25.9), $C_{12}$(28.3), $C_{2'a}$(124.5), $C_{2'b}$(135.7), $C_{3'a}$(115.9), $C_{3'b}$(107.6), $C_{6'a}$(122.7), $C_{6'b}$(121.9), $C_{7'a}$(112.5), $C_{7'b}$(111.9), $C_{8'a}$(127.5), $C_{8'b}$(128.2), $C_{9'b}$(137.7), $C_{9'a}$(137.9). Ion Spray (M$^+$) 459 Elemental analysis: (calculated) C, 73.34%; H, 6.59%; N, 6.11%. (found) C, 73.11%; H, 6.63%; N, 5.55%. Melting point: 204–206° C. (dec.)

EXAMPLE 11
ST 1381

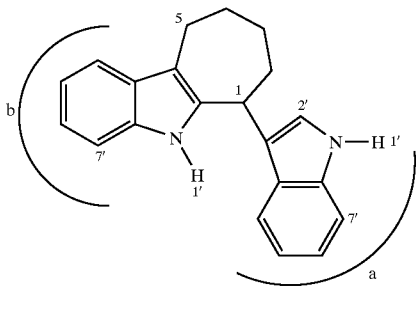

1-(indol-3-yl)-indo[2,3a]-cycloheptan.

TLC (Hexan/iPrOH=95/5): 0.22 HPLC RP-18 Waters 300×3.3 (40% H$_2$O, 60% CH$_3$CN, Flow 1 ml/min): 22.1

Racemic Mixture

NMR 300 MHz (H-1, DMSO-d6): H$_1$(4.65 br.s,1H)-H$_2$ (1.95 e 2.4 mm, 2H)-H$_3$(1.7 m, 2H)-H$_4$(1.6 e 1.9 mm, 2H)-H$_5$(2.75 e 3.0 mm, 2H)-H$_{2'a}$(6.68 s, 1H)-H$_{5'a}$-H$_{5'b}$(6.95 m, 2H)-H$_{6'a}$(7.07 t, 1H)-H$_{4'b}$(7.45 m, 1H)-H$_{7'b}$(7.2 m, 1H)-H$_{7'a}$(7.37 d, 1H)-H$_{4'a}$(7.52 d, 1H)-H$_{1'a}$(10.8 s,1H)-H$_{1'b}$(10.4 s, 1H). NMR 300 MHz (C-13, DMSO-d6): C$_1$(36.3), C$_2$(33.2), C$_3$(26.5), C$_4$(28.6), C$_5$(24.0), C$_{7'b}$(110.5), C$_{7'a}$ (111.4), C$_{3'a}$(115.6), C$_{4'b}$(117.2), C$_{5'b}$(117.7), C$_{5'a}$(118.2), C$_{4'a}$(118.5), C$_{6'b}$(119.7), C$_{6'a}$(120.7), C$_{2'a}$(123.5), C$_{8'a}$(125.9), C$_{8'b}$(128.6), C$_{9'b}$(134.2), C$_{9'a}$(136.6), C$_{2'b}$(139.7). Ion Spray (M$^-$): 299 Elemental analysis: (calculated) C, 83.96%; H, 6.71%; N, 9.33%. (found) C, 81.19%; H, 6.50%; N, 9.03% Melting point: 206–208° C.

EXAMPLE 12
ST 1621

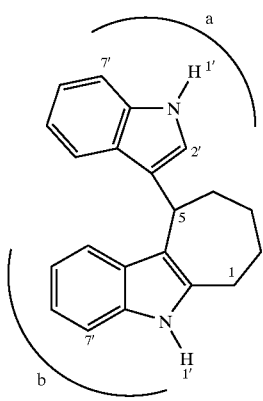

5-(indol-3-yl)-indo[2,3a]-cycloheptan.

TLC (Hexan/iPrOH=95/5): 0.15 HPLC RP-18 (40% H$_2$O, 60% CH$_3$CN, Flow 1 ml/min): 16.6

Racemic Mixture

NMR 300 MHz (H-1, DMSO-d6): H$_5$(4.8 br.s,1H)-H$_4$(1.9 and 2.4 mm, 2H)-H$_3$(1.5 and 1.7 mm, 2H)-H$_2$(1.5 and 1.9 mm, 2H)-H$_1$(2.9 br.s, 2H)-H$_{2'a}$(6.5 s, 1H)-H$_{5'b}$(6.8 t, 1H)-H$_{6'b}$(6.92 t, 1H)-H$_{5'a}$(6.97 t, 1H)-H$_{6'a}$(7.07 t, 1H)-H$_{4'b}$(7.13 d, 1H)-H$_{7'b}$(7.24 d, 1H)-H$_{7'a}$(7.3 d, 1H)-H$_{4'a}$(7.62 d, 1H)-H$_{1'a}$(10.6 s,1H)-H$_{1'b}$(10.7 s, 1H). NMR 300 MHz (C-13, DMSO-d6): C$_3$(25.2)-C$_2$(27.3)-C$_1$(28.3)-C$_5$(31.8)-C$_4$(33.7)-C$_{7'b}$(10.2)-C$_{7'a}$(111.3)-C$_{3'b}$(114.5)-C$_{4'b}$(117.1)-C$_{3'a}$(117.4)-C$_{5'b}$(117.7)-C$_{5'a}$(117.9)-C$_{4'a}$(118.6)-C$_{6'b}$(119.6)-C$_{6'a}$(120.5)-C$_{2'a}$(123.5)-C$_{8'a}$(126.2)-C$_{8'b}$(128.5)-C$_{9'b}$(134.3)-C$_{9'a}$(136.6)-C$_{2'b}$(137.4). Ion Spray (M$^-$): 299 Elemental analysis: (calculated) C, 83.96%; H, 6.71%; N, 9.33%, in accordance with the theoretical. Melting point: 170° C.

EXAMPLE 13
ST 1728

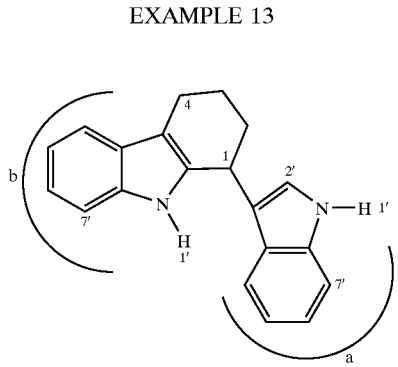

1-(1H-indol-3-yl)-tetrahydro-1H-carbazole

TLC (Hexane/iPrOH=9/1): 0.66 HPLC RP-18 (40% H$_2$O, 60% CH$_3$CN, Flow 1 ml/min): 18.4

Racemic Mixture

NMR 300 MHz (H-1, CD$_3$CN): H$_1$(4.46 t, 1H)-H$_2$(2.1 and 2.3 mm, 2H)-H$_3$(1.9 and 2.1 mm, 2H)-H$_4$(2.81 t, 2H)-H$_{2'a}$(6.98 s, 1H)-H$_{5'a}$(6.92 t, 1H)-H$_{5'b}$-H$_{6'b}$ (7.0 m, 2H)-H$_{6'a}$ (7.09 m, 1H)-H$_{7'b}$(7.15 m, 1H)-H$_{4'a}$(7.29 d, 1H)-H$_{7'a}$(7.4 dt, 1H)-H$_{4'b}$(7.46 d, 1H)-H$_{1'a}$(9.1 br.s, 1H)-H$_{1'b}$(8.6 br.s, 1H). NMR 300 MHz (C-13,, CD$_3$CN): C$_4$(21.8)-C$_3$(23.1)-C$_2$(33.0)-C$_1$(33.2)-C$_{3'b}$(110.6)-C$_{7'b}$(111.4)-C$_{7'a}$(112.3)-C$_{4'b}$(118.5)-C$_{3'a}$(118.7)-C$_{5'b}$(119.4)-C$_{5'a}$(119.7)-C$_{4'a}$(119.8)-C$_{6'b}$(121.5)-C$_{6'a}$(122.4)-C$_{2'a}$(123.9)-C$_{8'a}$(127.5)-C$_{8'b}$(128.6)-C$_{9'b}$(137.0)-C$_{9'a}$(137.8)-C$_{2'b}$(137.9). Ion Spray (M$^+$): 287 Elemental analysis: (calculated) C, 83.30%; H, 6.99%; N, 9.71%, in accordance with the theoretical. Melting point: 207° C.

EXAMPLE 14
ST 1729

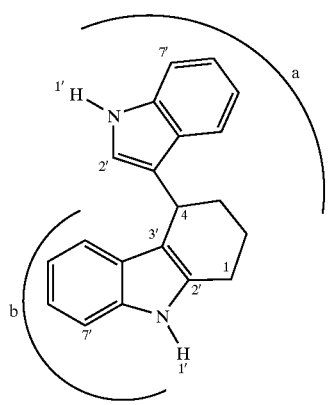

4-(1H-indol-3-yl)-tetrahydro-1H-carbazole

TLC (Hexane/iPrOH=9/1): 0.55 HPLC RP-18 (40% H$_2$O, 60% CH$_3$CN, Flow 1 ml/min): 12.4

Racemic Mixture

NMR 300 MHz (H-1, CD$_3$CN): H$_1$(2.83 m, 1H)-H$_2$(1.95 and 1.84 mm, 2H)-H$_3$(2.17 and 2.04 mm, 2H)-H$_4$(4.49 t, 1H)-H$_{2'a}$(6.77 d, 1H)-H$_{4'a}$(7.43 d, 1H)-H$_{6'a}$(7.06 t, 1H)-H$_{7'a}$ (7.36 d, 1H)-H$_{5'a}$(6.92 m, 1H)-H$_{7'b}$(7.27 d, 1H)-H$_{4'b}$(6.83 d, 1H)-H$_{5'a}$ (6.71 t, 1H)-H$_{6'b}$(6.94 m, 1H)-H$_{1'a}$(8.96 br, 1H)-

$H_{1'b}$(8.94 br, 1H). NMR 300 MHz (C-13, CD$_3$CN): $C_2$(22.0)-$C_1$(24.0)-$C_4$(31.0)-$C_3$(33.0)-$C_{7'b}$(111.3)-$C_{7'a}$(112.3)-$C_{3'b}$(112.5)-$C_{4'a}$(119.3)-$C_{3'a}$(120.9)-$C_{6'b}$(121.2)-$C_{6'a}$(122.1)-$C_{2'a}$(123.7)-$C_{8'a}$(127.7)-$C_{8'b}$(128.5)-$C_{2'b}$(136.2)-$C_{9'b}$(137.0)-$C_{9'a}$(137.8). Ion Spray (M$^+$): 287 Elemental analysis: (calculated) C, 83.30%; H, 6.99%; N, 9.71%. Melting point: 182° C.

EXAMPLE 15
ST 1749

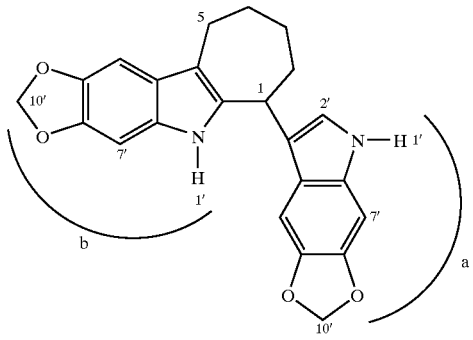

1-(5",6"-methylendioxy-indol-3-yl)-5',6'-methyleridioxy-indo[2,3-a]-cycloeptane

TLC (Hexane/AcOEt=8/2): 0.23 HPLC RP-18 (40% H$_2$O, 60% CH$_3$CN, Flow 1 ml/min): 15.4

Racemic Mixture

NMR 300 MHz (H-1, CD$_3$CN): $H_1$(4.45 m, 1H)-$H_2$(2.05 and 2.25 mm, 2H)-$H_3$–$H_4$ (1.8 m, 4H)-$H_5$(2.85 m, 2H)-$H_{10'b}$(5.85 d, 1H)-$H_{10'a}$(5.90 s, 2H)-$H_{7'b}$(6.66 s, 1H)-$H_{2'a}$(6.8 d, 1H)-$H_{4'b}$(8.3 s, 1H)-$H_{4'a}$(6.9 s, 1H)-$H_{7'a}$(6.94 s, 1H)-$H_{1'b}$ (8.4 s, 1H)-$H_{1'a}$(9.0 s,1H). NMR 300 MHz (C-13, CD$_3$CN): $C_5$(25.4), $C_3$–$C_4$(29.5), $C_2$(35.3), $C_1$(38.1), $C_{7'b}$(92.4), $C_{7'a}$(93.0), $C_{4'a}$(97.3), $C_{4'b}$(98.4), $C_{10'b}$(101.1), $C_{10'a}$(101.5), $C_{3'b}$(113.4), $C_{3'a}$(118.2), $C_{8'a}$(121.3), $C_{2'a}$(121.7), $C_{8'b}$(124.0), $C_{9'b}$(129.8), $C_{9'a}$(132.7), $C_{2'b}$(139.3), $C_{6'b}$(142.9), $C_{6'a}$(143.3), $C_{5'b}$(144.3), $C_{5'a}$(145.5). Ion Spray (M$^+$):389 Elemental analysis: (calculated) C, 71.12%; H, 5.19%; N, 7.21%. (found) in accordance with the theoretical. Melting point: 184° C. (dec.)

EXAMPLE 16
ST 1751

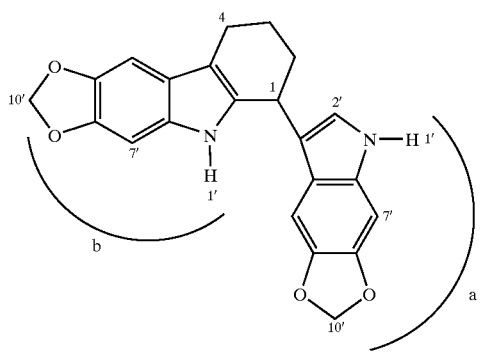

1-(5',6'-methylendioxy-1H-indol-3-yl)-6,7-methylendioxy-tetrahydro-1H-carbazole

TLC (Hexane/iPrOH=9/1): 0.31 HPLC RP-18 (40% H$_2$O, 60% CH$_3$CN, Flow 1 ml/min): 11.5

Racemic Mixture

NMR 300 MHz (H-1, CD$_3$CN): $H_1$(4.32 t, 1H)-$H_2$(2.2 and 2.0 mm, 2H)-$H_3$(2.03 and 1.83 mm, 2H)-$H_4$(4.3 t, 2H)-$H_{10'a}$–$H_{10'b}$(5.8–5.9 dd, 4H)-$H_{4'a}$(6.65 s, 1H)-$H_{7'b}$(6.72 s, 1H)-$H_{2'a}$(6.88 d, 1H)-$H_{7'a}$–$H_{4'b}$(6.90 s, 1H)-$H_{1'b}$(8.4 s, 1H)-$H_{1'a}$(9.0 s, 1H). NMR 300 MHz (C-13, CD$_3$CN): $C_4$(21.8)-$C_3$(23.2)-$C_2$(33.0)-$C_1$(33.3)-$C_{7'b}$(92.8)-$C_{7'a}$(93.0)-$C_{4'b}$(97.6)-$C_{4'a}$(98.2)-$C_{10'a}$(101.2)-$C_{10'b}$(101.5)-$C_{3'b}$(110.8)-$C_{3'a}$(119.1)-$C_{8'a}$(121.4)-$C_{2'a}$–$C_{8'b}$(122.4)-$C_{9'b}$(131.6)-$C_{9'a}$(132.6)-$C_{2'b}$(136.6)-$C_{6'b}$(142.9)-$C_{6'a}$(143.2)-$C_{5'b}$(144.6)-$C_{5'a}$(145.4). Ion Spray (M$^+$): 375 Elemental analysis: (calculated) C, 70.58%; H, 4.85%; N, 7.48%, in accordance with the theoretical. Melting point: 200° C. (dec.)

EXAMPLE 17
ST 1765

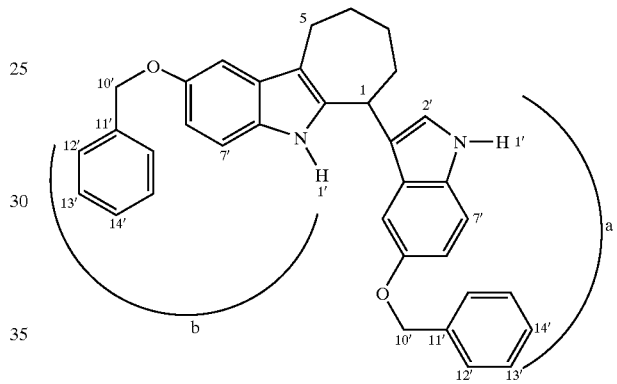

1-(5"-benzyloxy-indol-3-yl)-5'-benzyloxy-indo[2,3a]-cycloheptan.

TLC (Hexan/iPrOH=9/1): 0.62 HPLC RP-18 (40% H$_2$O, 60% CH$_3$CN, Flow 1 ml/min): 27.1

Racemic Mixture

NMR 300 MHz (H-1, CD$_3$CN): $H_1$(4.54 d, 1H)-$H_2$(2.32 and 2.08 mm, 2H)-$H_3$(1.83 m, 2H)-$H_4$(1.83 m, 2H)-$H_5$(2.88 m, 2H)-$H_{10'a}$(4.99 s, 2H)-$H_{10'b}$(5.13 s, 2H)-$H_{5'a}$–$H_{5'b}$(6.95 m, 2H)-$H_{6'b}$(6.74 q, 1H)-$H_{6'a}$(6.87 q, 1H)-$H_{2'a}$(6.90 d, 1H)-$H_{4'a}$(6.93 d, 1H)-$H_{7'b}$(7.07 d, 1H)-$H_{4'b}$(7.09 d, 1H)-$H_{14'a}$–$H_{14'b}$(7.31–7.27 m, 2H)-$H_{7'a}$(7.34 m, 1H)-$H_{13'a}$(7.33 m, 1H)-$H_{13'b}$(7.38 m, 1H)-$H_{12'a}$(7.39 d, 1H)-$H_{12'b}$(7.47 d, 1H)-$H_{1'b}$(8.47 s,1H)-$H_{1'a}$(9.0 s, 1H). NMR 300 MHz (C-13, CD$_3$CN): $C_1$(38.01), $C_2$(35.1), $C_3$(29.5), $C_4$(29.4), $C_5$(25.3), $C_{10'a}$(71.3) $C_{10'b}$(71.4), $C_{4'b}$(102.5), $C_{4'a}$(103.7), $C_{6'b}$ (111.7), $C_{7'b}$(112.0), $C_{7'a}$(113.1), $C_{3'b}$–$C_{6'a}$ (113.2), $C_{3'a}$ (117.4), $C_{2'a}$(125.0), $C_{8'a}$(127.9), $C_{12'b}$(128.5), $C_{12'a}$(128.6), $C_{13'a}$(129.3), $C_{13'b}$(129.4), $C_{8'b}$(130.5), $C_{9'b}$(130.7), $C_{9'a}$ (133.2), $C_{11'a}$(139.0), $C_{11'b}$(139.3), $C_{2'b}$(141.7), $C_{7'a}$(113.0), $C_{6'a}$-$C_{3'a}$ (113.2), $C_{14'a}$-$C_{14'b}$-$C_{12'b}$ (128.5), $C_{12'a}$(128.6) Ion Spray (M$^+$): 513 Elemental analysis: (calculated) C, 82.00%; H, 6.29%; N, 5.46%.—(found) in accordance with the theoretical. Melting point: 286° C. (dec.)

EXAMPLE 18
ST 1777

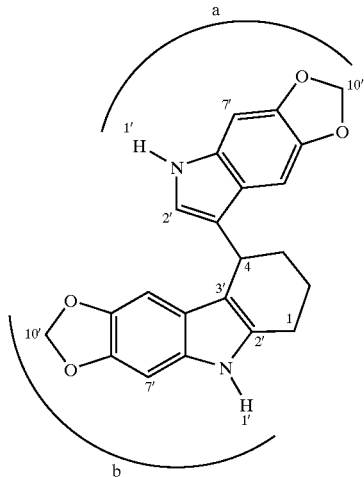

4-(5',6'-methylendioxy-1H-indol-3-yl)-6,7-methylendioxy-tetrahydro-1H-carbazole

TLC (Hexane/iPrOH=9/1): 0.20 HPLC RP-18 (40% $H_2O$, 60% $CH_3CN$, Flow 1 ml/min): 7.9

Racemic Mixture

NMR 300 MHz (H-1, $CD_3CN$): $H_1$(2.80, 1H)-$H_2$(1.96 and 1.84 mm, 2H)-$H_3$(2.13 and 1. mm, 2H)-$H_4$(4.31 t, 1H)-$H_{10'b}$(5.76 d, 2H)-$H_{10'a}$(5.86 d, 2H)-$H_{4'b}$(6.22 s, 1H)-$H_{4'a}$(6.74 s, 1H)-$H_{2'a}$(6.75 d, 1H)-$H_{7'b}$(6.82 s, 1H)-$H_{7'a}$(6.88 s, 1H)-$H_{1'b}$(8.83 s, 1H)-$H_{1'a}$(8.86 s, 1H). NMR 300 MHz (C-13, $CD_3CN$): $C_2$(22.3)-$C_1$(23.9)-$C_4$(31.7)-$C_3$(33.1)-$C_{7'b}$(92.7)-$C_{7'a}$(93.0)-$C_{4'b}$(98.3)-$C_{4'a}$(98.5)-$C_{10'b}$(101.1)-$C_{10'a}$(101.4)-$C_{3'b}$(112.8)-$C_{3'a}$(120.9)-$C_{8'a}$(121.5)-$C_{8'b}$–$C_{2'b}$(122.3)-$C_{9'b}$(131.6)-$C_{9'a}$(132.6)-$C_{2'b}$(134.7)-$C_{6'b}$(142.4)-$C_{6'a}$(142.9)-$C_{5'b}$(144.2)-$C_{5'a}$(145.2). Ion Spray ($M^-$): 373 Elemental analysis: (Calculated) C, 70.20%; H, 5.36%; N, 7.44%, in accordance with the theoretical. Melting point: 228° C. (dec.)

EXAMPLE 19
ST 1778

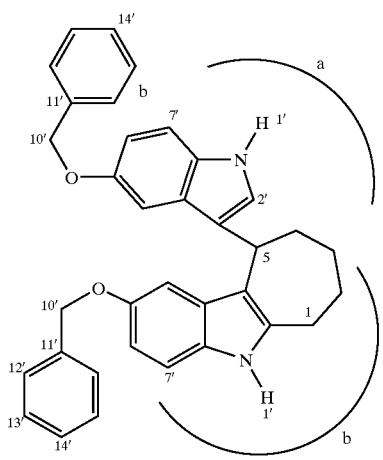

5-(5"-benzyloxy-indol-3-yl)-5'-benzyloxy-indo[2,3a]-cycloheptan.

TLC (Hexane/iPrOH=9/1): 0.4 HPLC RP-18 (40% $H_2O$, 60% $CH_3CN$, Flow 1 ml/min): 18.1

Racemic Mixture

NMR 300 MHz (H-1, $CD_3CN$): $H_1$(2.89 m,1H)-$H_4$(2.49 m, 2H)-$H_3$(1.6 and 1.8 mm, 2H)-$H_2$(1.6 m, 2H)-$H_5$(4.72 t, 1H)-$H_{10'b}$(4.89 d, 2H)-$H_{10'a}$(5.08 s, 2H)-$H_{2'a}$(6.54 d, 1H)-$H_{6'b}$(6.68 q, 1H)-$H_{4'b}$(6.75 d, 1H)-$H_{6'a}$(6.83 q, 1H)-$H_{7'b}$(7.16 d, 1H)-$H_{4'a}$(7.16 d, 1H)-$H_{7'a}$(7.28 d, 1H)-$H_{13'b}$(7.29 m, 1H)-$H_{12'b}$(7.34 m,1H)-$H_{13'a}$(7.37 m, 1H)-$H_{12'a}$(7.47 d, 1H)-$H_{1'a}$(8.90 s, 1H)-$H_{1'b}$(8.93 s, 1H). NMR 300 MHz (C-13, $CD_3CN$): $C_3$(26.6)-$C_2$(28.5)-$C_1$(29.7)-$C_5$(33.4)-$C_4$(34.7)-$C_{10'b}$(71.2)-$C_{10'a}$(71.4)-$C_{4'b}$(112.5)-$C_{4'a}$(104.0)-$C_{6'b}$(111.6)-$C_{6'a}$(111.8)-$C_{7'b}$(112.9)-$C_{7'a}$(112.9)-$C_{3'b}$(116.1)-$C_{3'a}$(119.2)-$C_{2'a}$(125.3)-$C_{8'a}$(128.1)-$C_{14'b}$(128.5)-$C_{14'a}$(128.6)-$C_{12'b}$(128.6)-$C_{12'a}$(128.7)-$C_{13'a}$(129.2)-$C_{13'b}$(129.3)-$C_{8'b}$(130.5)-$C_{9'b}$(131.0)-$C_{9'a}$(133.3)-$C_{11'a}$–$C_{11'b}$(139.1)-$C_{2'b}$(139.7)-$C_{5'a}$(153.3)-$C_{5'b}$(153.5). Ion Spray ($M^-$): 511 Elemental analysis: (calculated) C, 82.00%; H, 6.29%; N, 5.46%, in accordance with the theoretical. Melting point: 237° C. (dec.)

EXAMPLE 20
ST1783

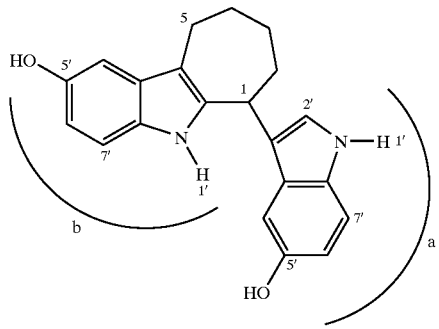

1-(5"-hydroxy-1H-indol-3-yl)-5'-hydroxy-indo[2,3a]-cycloheptan.

TLC (Hexane/iPrOH=9/1): 0.35 HPLC RP-18 Waters 300×3.3 (45% $H_2O$, 55% $CH_3CN$, Flow 1 ml/min): 4.2

Racemic Mixture

NMR 300 MHz (H-1, $CD_3CN$): $H_1$(4.61 d, 1H)-$H_2$(2.3 and 2.0 mm, 2H)-$H_3$(1.9 m, 2H)-$H_4$(1.8 m, 2H)-$H_5$(2.97 m, 2H)-OH(6.45 br.d, 2H)-$H_{7'b}$(6.67 d, 1H)-$H_{7'a}$(6.83 d, 1H)-$H_{4'a}$ $H_{4'b}$(6.95 s, 2H)-$H_{2'a}$(7.0 s, 1H)-$H_{6'b}$(7.1 d, 1H)-$H_{6'a}$(6.4 d, 1H)-$H_{1'b}$(8.44 s,1H)-$H_{1'a}$(9.01 s, 1H). NMR 300 MHz (C-13, $CD_3CN$): $C_1$(36.6), $C_2$(33.6), $C_3$(28.1), $C_4$(28.0), $C_5$(23.8), $C_{4'b}$(101.1), $C_{4'a}$(102.4), $C_{6'b}$(109.1), $C_{7'b}$(110.1), $C_{7'a}$(110.7), $C_{3'b}$–$C_{6'a}$ (111.0), $C_{3'a}$(115.3), $C_{2'a}$(126.5), $C_{8'a}$(128.4), $C_{8'b}$(128.6), $C_{9'b}$(129.2), $C_{9'a}$(131.0), $C_{2'b}$(140.1), $C_{5'a}$–$C_{5'b}$(149.3). Ion Spray ($M^+$): 333 Elemental analysis: (calculated) C, 75.88%; H, 6.06%; N, 8.43%. (found) in accordance with the theoretical.

EXAMPLE 21

In the similar way were prepared the following compounds:

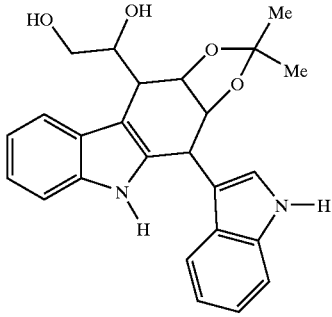

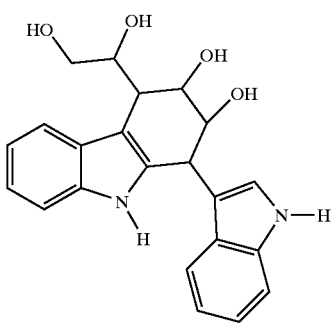

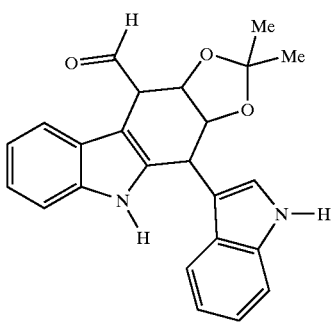

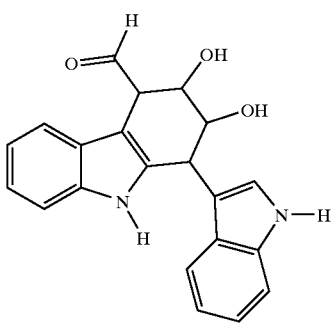

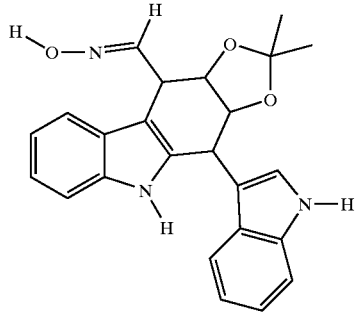

| COMPOUND | PROCEDURE | NOTE |
|---|---|---|
| ST1866 | A | Bis-7-azaindolyl via magnesiumbromide |
| ST1345 | B | Bis-indolyl via acid catalysis |
| ST1346 | B | " |
| ST1422 | B | " |
| ST1423 | B | " |
| ST1707 | B | " |
| ST1750 | B | " |
| ST1372 | C | Cyclization of sugar moieties |
| ST1381 | D | Cyclization of the non-sugar moieties |
| ST1621 | D | " |
| ST1728 | D | " |
| ST1729 | D | " |
| ST1749 | D | " |
| ST1751 | D | " |
| ST1765 | D | " |
| ST1777 | D | " |
| ST1778 | D | " |
| ST1783 | E | Debenzylation |
| ST1900 | F | Deprotection |
| ST1901 | F | Deprotection |
| ST (all) | G | Oxydation |

Pharmacology

The abbreviation ST, followed by a number, identifies the compounds figuring in the examples reported in the pharmacological assays.

For the antiangiogenic activity the chemotactic assay with the Boyden chamber was performed (Werner F., Goodwin R. H. and Leonard E. J., Journal of Immunological Methods 1980; 33, 239–247), using both bovine aortal endothelial cell (BAEC) cultures and bovine medullary endothelial cell (BMEC) cultures. The assays were performed at $IC_0$ (maximum non-cytotoxic concentration) and the results expressed as % inhibition of migration across a porous filter in response to a chemotactic stimulus (1% bovine serum in DMEM culture medium). This finding was obtained by direct cell count under the optical microscope, and the percentage migration inhibition was calculated according to the formula $(T-C/C)\times 100$, where T=mean number of cells migrating in the sample and C=mean number of cells migrating in the control. The control consisted of cells which migrated towards the serum, not treated with the study molecules, and included in every chemotaxis experiment. The data refer to the readings of 5 microscopic fields/well in 4 independent chemotaxis wells per sample. The results obtained are reported on Table 4.

For the cytotoxic activity, proliferation screening tests were used, with different tumour lines, such as MCF-7 (human mammary carcinoma), LoVo (human colon carcinoma), MES-SA (human uterine sarcoma), or K-562 (human chronic myeloid leukaemia).

The test used was the sulforodamine B test used for screening anticancer products at the National Cancer Institute (Skehan, 1990). The molecules at scalar concentrations over a range from 500 $\mu$M to 0.97 $\mu$M, were incubated in parallel with different human cell lines for 24 hours. After removing the products, cell survival was investigated after another 48 hours with the NCI test. The antiproliferative capacity of the compounds was quantified in terms of $IC_{50} \pm SD$ (concentration of the molecule that inhibits 50% of cell survival) processed using a curve fitting program (De Lean et al., 1978). The results obtained are reported on Table 1 and Table 2.

The cell cycle and apoptosis analysis on a tumour line was done by incubating the products for 24 hours at a concentration equal to approximately the $IC_{50}$ values with MCF-7 cells. The molecules were removed and the cell cycle and apoptosis were assessed at different times (0, 24, 48 hours). The cells were stained with propidium iodide and analysed with a cytofluorimeter (FACS) (Beckman Dickinson fluorescence activated cell sorter) by means of an argon ion laser set at 488 nm for the excitation. To assess the percentage of cells in the various stages of the cycle, linear DNA histograms were analysed with a cell fit program distributed by the equipment manufacturer. For the analysis of apoptosis, a region was inserted below the G0/G1 peak of the control population and the data were analysed with software supplied by the company (Lysis II-C32). The results obtained are reported on Table 3.

The cytotoxicity of the molecules on tumour lines resistant to chemosensitising activity was assessed on various tumour cell lines overexpressing P-glycoprotein and resistant to doxorubicin (100-fold) and cross-resistant to daunorubicin, actinomycin D, mitoxantrone, vincristine, vinblastine, taxol, colchicine, and etoposide. The cytotoxicity of the products was assessed using the same test adopted for the sensitive tumour cells.

Later, the products were assayed at a concentration lower than or equal to the one that inhibits 10% of cell survival. At this concentration, the molecules were tested in parallel in the absence and presence of doxorubicin. MDR ratios were calculated for the $IC_{50}$ values in order to establish the degree of potentiation of the cytotoxic activity of doxorubicin induced by the product (MDR ratio) (De Lean et al. (1978) A. J. Physiol. 235, E97–102); (Skehan et al. (1990) J. Natl. Cancer Inst. 82, 1107–1112).

TABLE 1

ANTIPROLIFERATIVE ACTIVITY vs SENSITIVE CELL

| | | $IC_{50}$ +/− SD ($\mu$M) | |
|---|---|---|---|
| Series | Compound | MCF-7 | LoVo |
| Tetrahydrocarbazoles | ST1372 | 21.1 +/− 0.3 | 21.7 +/− 4.3 |
| " | ST1728 | 22 +/− 2.8 | 22.8 +/− 2.9 |
| " | ST1729 | 35 +/− 6.1 | 50.5 +/− 4.8 |
| " | ST1777 | 0.96 +/− 0.19 | 0.64 +/− 0.003 |
| Esahydrocycloept[b]indoles | ST1381 | 28.5 +/− 1.8 | 22.5 +/− 2.6 |
| " | ST1621 | 22.5 +/− 1.3 | 34.8 +/− 4.3 |
| " | ST1765 | 11.5 +/− 1.1 | 10.5 +/− 0.07 |
| " | ST1778 | 28.5 +/− 1.4 | 54.5 +/− 7.4 |
| " | ST1783 | 27 +/− 4 | 29 +/− 0.06 |

TABLE 2

ANTIPROLIFERATIVE ACTIVITY vs RESISTENT CELL

| | | $IC_{50}$ +/− SD ($\mu$M) | |
|---|---|---|---|
| Series | Compound | MCF-7/DX | LoVo/DX |
| Tetrahydrocarbazoles | ST1372 | 26.9 +/− 1.6 | 26.3 +/− 3.7 |
| " | ST1751 | 58.6 +/− 9 | |
| EsahydroCycloept[b]indoles | ST1381 | 28.4 +/− 3 | 25.2 +/− 4.2 |
| " | ST1621 | 68.3 +/− 4.6 | 23.8 +/− 3.7 |
| " | ST1765 | 24.8 +/− 3.8 | 17.03 +/− 0.91 |
| " | ST1778 | 71 +/− 0.4 | 65.1 +/− 8.1 |
| " | ST1783 | 39 +/− 0.03 | |

TABLE 3

CELLULAR CYCLE AND APOPTOSIS ON MCF-7 CELL

| Compound | G0/G1 (%) | S (%) | G2 + M (%) | Apoptosis 48 h (%) |
|---|---|---|---|---|
| ST1372 | C = 43.7 | C = 47.6 | C = 8.6 | C = 3.3 |
| | 40 $\mu$M = 57.8 | 40 $\mu$M = 36.8 | 40 $\mu$M = 5.4 | 40 $\mu$M = 16 |
| | 20 $\mu$M = 54.4 | 20 $\mu$M = 34.2 | 20 $\mu$M = 11.4 | |
| ST1381 | C = 43.8 | C = 47.6 | C = 8.6 | C = 3.3 |
| | 30 $\mu$M = 57.7 | 30 $\mu$M = 32.2 | 30 $\mu$M = 10.1 | 30 $\mu$M = 3.3 |

ST1372 at 40 μM increases and blocks in G0/G1 32% of the cell, and at 20 μM increases and blocks in G0/G1 23% of the cell.

ST1372 at 11 μM increases 3.5 times the activity of the Doxorubicin both on MCF-7/Dx line and on LoVo/Dx cell line.

ST1381 at 30 μM increases and blocked in G0/G1 32% of the cell line; is not cytotoxic vs endotelial cell (IC>100 μM); and is active for the chemotaxys.

TABLE 4

CYTOTOXYCITY AND CHEMOTAXYS ON BMEC

| | | MEC | | |
|---|---|---|---|---|
| Series | Compound | $IC_{50}$ (μM) | $IC_0$ (μM) | % inhibition of migration at $IC_0$/D.S. |
| Esahydrocycloept[b]indoles | ST1381 | >100 | 30 | −61.7 +/− 6.3 |
| " | ST1621 | 10 | 0.1 | −43 +/− 4 |
| " | ST1749 | >200 | 100 | −40 +/− 3 |
| " | ST1778 | 50 | 25 | −40 +/− 4 |
| " | ST1783 | 60 | 10 | −46 |
| " | ST1729 | 80 | 25 | −40 +/− 3 |

Although ST 1381 results the better anti-chemiotactic compound, is important to note that all compounds of this group decrease the chemiotaxis of endothelial cells.

The composition according to the invention contain as active ingredient at least one formula (I) alone or in combination with other active ingredients useful in the treatment of the diseases indicated in the invention described herein, in the form of separate doses or in forms suitable for combined therapies. The active ingredient according to the invention will be in a mixture with appropriate vehicles and/or excipients commonly used in pharmacy, such as, for instance, those described in "Remington's Pharmaceutical Sciences Handbook", latest edition. The compositions according to the invention will contain a therapeutically effective amount of the active ingredient. The doses will be determined by the expert in the sector, for example the clinician or primary-care physician, according to the type of disease to be treated and the patient's condition, or concomitantly in conjunction with the administration of other active ingredients.

Examples of pharmaceutical compositions are those that allow oral or parenteral, intravenous, intramuscular, subcutaneous or transdermal administration. Pharmaceutical compositions suitable for the purpose are tablets, rigid or soft capsules, powders, solutions, suspensions, syrups, and solid forms for extempore liquid preparations. Compositions for parenteral administration are, for example, all the intramuscular, intravenous, and subcutaneous injectable forms, in the form of solutions, suspensions or emulsions. Also worthy of mention are the liposomal formulations. Suitable compositions also include forms based on slow release of the active ingredient, whether as oral administration forms, tablets coated with suitable layers, microencapsulated powders, cyclodextrine complexes, or depot forms. e.g. subcutaneous, such as depot injections or implants.

What is claimed is:

1. A compound having the formula (I):

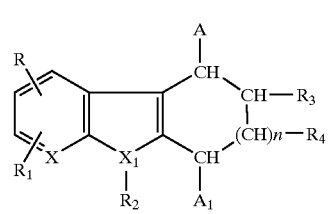

(I)

wherein:

X=CH $X_1$=N

R and $R_1$, which are the same or different, are selected from the group consisting of —H, OH, $OR_5$ in which $R_5$ may be $C_1$–$C_4$ alkyl or benzyl, when two groups $OR_5$ are vicinal $R_5$ is methylene; or R and $R_1$ may be independently nitro; amino optionally mono- or di-substituted with $C_1$–$C_4$ alkyl; carboxy; or alkoxy ($C_1$–$C_4$) carbonyl;

R and $R_1$ taken together form an aliphatic or aromatic cyclic group having 5 or 6 atoms;

$R_2$ is selected from the group consisting of —H, phenyl, benzyl, linear or branched $C_1$–$C_6$ alkyl;

n=is an integer ranging from 0 and 4;

$R_3$, which is the same as or different from $R_4$, is —H, —OH, —$OR_6$, wherein $R_6$ is linear or branched $C_1$–$C_4$ alkyl, or when $R_3$=$R_4$=$OR_6$ vicinal, $R_6$ is isopropylidene

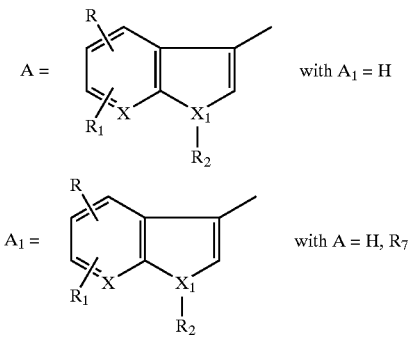

$R_7$=$C_1$–$C_4$ linear or branched alkyl optionally substituted with one or two groups OH, $OR_6$, in case of 2 groups $OR_6$ vicinal, $R_6$ is isopropylidene; or $R_7$ is formyl (CHO), oxime (CH=NOH), their isomers and their mixtures.

2. A pharmaceutical composition containing as active ingredient a compound of claim 1, and at least a pharmaceutically acceptable excipient and/or diluent.

3. A combination consisting of
   (a) a compound of formula (I) as claimed in claim 1 with
   (b) an anticancer drug, in which the anticancer drug is selected from the group consisting of alkylating agents, topoisomerase inhibitors, antitubulin agents, intercalating compounds, anti-metabolites, natural products, epipodophyllotoxins, antibiotics, enzymes, taxans, cyto-differentiating compounds and anti-angiogenic compounds.

4. A pharmaceutical composition comprising as active ingredient the combination of claim 3 and one or more pharmacologically acceptable excipients or vehicles.

5. The composition of claim 4, wherein the compound of formula (I) is present as a co-adjuvant of the anticancer compound.

6. The composition of claim 4, wherein the compound of formula (I) and the anticancer drugs are administered simultaneously or sequentially.

7. The composition of claim 2 or 4, in the form of tablets, capsules, powders, solutions, suspensions, vials, syrups, suppository, enema, foam or liposomal formulations, useful for oral, parenteral or rectal administration.

8. A method of treating mammary carcinoma or colon carcinoma comprising administering to a subject in need thereof a therapeutically effective amount of a compound of claim 1.

* * * * *